United States Patent [19]

Hamada et al.

[11] Patent Number: 4,659,549
[45] Date of Patent: Apr. 21, 1987

[54] BLOOD OXYGENATOR USING A HOLLOW FIBER MEMBRANE

[75] Inventors: Eiichi Hamada; Atushi Nakashima; Jun Kamo, all of Otake, Japan

[73] Assignee: Mitsubishi Rayon Co., Ltd., Tokyo, Japan

[21] Appl. No.: 682,858

[22] Filed: Dec. 18, 1984

[30] Foreign Application Priority Data

Mar. 14, 1984 [JP] Japan .................................. 59-48793

[51] Int. Cl.$^4$ .......................... A61M 1/14; A61M 1/18; B01D 13/00
[52] U.S. Cl. .................................. 422/48; 210/321.3; 210/321.4; 128/DIG. 3
[58] Field of Search ............ 422/48; 210/321.3, 321.4; 128/DIG. 3; 55/158

[56] References Cited

U.S. PATENT DOCUMENTS

| | | | |
|---|---|---|---|
| 2,972,349 | 2/1961 | De Wall | 422/48 |
| 3,728,256 | 6/1971 | Cooper | 210/321.3 X |
| 3,998,593 | 12/1976 | Yoshida et al. | 422/46 |
| 4,231,878 | 11/1980 | Esmond | 422/48 X |
| 4,376,095 | 3/1983 | Hasegawa | 422/48 X |

Primary Examiner—Barry S. Richman
Assistant Examiner—Lynn M. Kummert
Attorney, Agent, or Firm—Oblon, Fisher, Spivak, McClelland & Maier

[57] ABSTRACT

A blood oxygenator comprising a housing generally in the form of a box and bundles of hollow fibers of semipermeable membrane set therein for effecting gas exchange therethrough. In this blood oxygenator, each end of each bundle of hollow fibers of semipermeable membrane is secured together by potting material in such a way as to allow their open ends to communicate separately with a gas inlet and a gas outlet; the space around the bundles of hollow fibers of semipermeable membrane communicates with a blood inlet and a blood outlet; the blood-gas contact chamber within the housing is divided into a plurality of compartments with the interposition of blood flow channels narrowed by baffles; and the bundle of hollow fibers of semipermeable membrane is disposed in the contact chamber so as to be substantially parallel to the baffles. This blood oxygenator has high oxygen and carbon dioxide exchange rates per unit area of membrane, causes little channeling of the blood and gas, exhibits only a small pressure loss in the flow of blood, and is easy to manufacture.

7 Claims, 8 Drawing Figures (a)   (b)   (c)

BLOOD OXYGENATOR USING A HOLLOW FIBER MEMBRANE

BACKGROUND OF THE INVENTION

1. Field of the Invention

This invention relates to a blood oxygenator of the outside perfusion type using a hollow fiber membrane.

2. Description of the Prior Art

A number of blood oxygenators using a hollow fiber membrane have already been proposed, for example, in U.S. Pat. Nos. 2,972,349, 3,794,468, 4,239,729 and 4,374,802.

In these blood oxygenators, homogeneous hollow fiber membrane composed of a gas-permeable material such as silicone or microporous hollow fiber membrane composed of a hydrophobic polymeric material such as a polyolefin are used to bring blood into contact with gas through the medium of the hollow fiber membrane and to effect gas exchange therebetween There are two types of blood oxygenators: the inside perfusion type in which blood is passed through the bores of the hollow fibers while gas is passed on the outside of the hollow fiber and the outside perfusion type in which, conversely, gas is passed through the bores of the hollow fibers while blood is passed on the outside of the hollow fibers.

In most of the conventionally known blood oxygenators, a cylindrical housing is simply packed with a large number of semipermeable hollow fiber membrane for use in gas exchange in such a way that the hollow fibers are parallel to the axis of the cylindrical housing. However, blood oxygenators of this construction have a low gas exchange rate per unit area of hollow fiber membrane, whether they are of the inside perfusion type or of the outside perfusion type. As an improved form of the outside perfusion type, U.S. Pat. No. 3,794,468 has proposed a blood oxygenator in which hollow tubular conduits of semipermeable membrane are wound about a hollow, cylindrical core having a large number of pores in the wall and then contained in a housing, and blood is allowed to flow out of the cavity of the core through its pores while gas is passed through the bores of the hollow tubular conduits.

In blood oxygenators of the inside perfusion type in which gas exchange is effected by passing blood through the bores of the hollow fibers while passing gas on the outside of the hollow fibers, channeling of the blood occurs less frequently. However, since the blood flowing through the bores of the hollow fibers moves in a laminar flow, the internal diameter of the hollow fibers needs to be reduced in order to increase the oxygenation rate (i.e., the oxygen transfer rate per unit area of membrane). For this purpose, semipermeable hollow fiber membrane having an internal diameter of the order of 150–300 $\mu$m have been developed for use in blood oxygenators.

However, as long as the blood moves in a laminar flow, the oxygenation rate cannot be greatly increased by reducing the internal diameter. Moreover, as the internal diameter becomes smaller, clotting (i.e., blockage of the bore due to the coagulation of blood) may occur more frequently and/or the blood will be more subject to hemolysis due to an increased pressure loss through the oxygenator, thus posing serious problems from a practical point of view. Further, since a blood oxygenator generally uses tens of thousands of hollow fibers of semipermeable membrane made into a bundle or bundles, special consideration must be given so as to distribute the gas uniformly to the external surfaces of each of these numerous hollow fibers. If the gas is not distributed uniformly, the carbon dioxide desorption rate (i.e., the carbon dioxide transfer rate per unit area of membrane) will be reduced. On the other hand, in blood oxygenators of the outside perfusion type in which gas is passed through the bores of the hollow fibers while blood is passed on the outside of the hollow fibers, the gas can be distributed uniformly and the blood can be expected to move not in a laminar flow. However, these oxygenators have the disadvantage of being subject to insufficient oxygenation due to channeling of the blood and/or blood coagulation at the sites of stagnation. Although the blood oxygenator of the aforementioned U.S. Pat. No. 3,794,468 has undergone improvements in this respect, it is still disadvantageous in that the priming volume of blood is excessively large, a considerable pressure loss through the oxygenator is caused, and a complicated procedure is required for its manufacture. Thus, it remains desirable to develop a more improved blood oxygenator.

SUMMARY OF THE INVENTION

The present invention has been made in view of the above-described circumstances, and it is therefore an object of the invention to provide a blood oxygenator module which exhibits only a small pressure loss, has a high oxygenation rate and a high carbon dioxide desorption rate, causes little stagnation or channeling of the blood, and can be manufactured without requiring any complicated procedure.

According to the present invention, there is provided a blood oxygenator comprising (1) a housing having a blood inlet, a blood outlet, a gas inlet and a gas outlet, and (2) bundles of semipermeable hollow fiber membrane set therein for effecting gas exchange therethrough, characterized in that said housing is generally in the form of a box; each end of said bundles of semipermeable hollow fiber membrane is secured together by means of a potting material in such a way as to allow their open ends to communicate separately with said gas inlet and gas outlet; the space around said bundles of semipermeable hollow fiber membrane communicate with said blood inlet and blood outlet; the blood-gas contact chamber within said housing is divided into a plurality of compartments with the interposition of blood flow channels narrowed by baffles; and said bundles of semipermeable hollow fiber membrane are disposed in said contact chamber so as to be substantially parallel to said baffles.

The degree of packing of the hollow fibers in each compartment of the contact chamber preferably ranges from 10 to 55% and more preferably from 20 to 40%. The term "degree of packing" as used herein means the percentage of the total cross-sectional area of the hollow fibers to the cross-sectional area of the compartment, as viewed in a plane perpendicular to the longitudinal axis of the bundle of hollow fibers. If the degree of packing is less than 10%, channeling of the blood will tend to occur, while if it is greater than 55%, the flow resistance of the blood may become excessively high, tending to cause a great pressure loss through the oxygenator and induce hemolysis. Although the degree of packing of the hollow fibers may vary with the compartment, it is preferable for convenience of manufacture to equalize the degree of packing.

The bundle of hollow fibers contained in the contact chamber should preferably be such that each hollow fiber is disposed parallel to the longitudinal axis of the bundle of hollow fibers. However, each hollow fiber may be wound at an angle of 10° to 45° with the longitudinal axis of the bundle of hollow fibers. The baffles dividing the contact chamber into compartments are disposed in a direction traversing the direction of blood flow, and the bundle of hollow fibers is disposed parallel to these baffles. The angle which the direction of blood flow forms with the bundle of hollow fibers must be in the range of 45° to 90° in order to prevent channeling of the blood. It is most preferable that the direction of blood flow be substantially perpendicular to the bundle of hollow fibers. The reason for this is believed to be that, when the blood flows across the hollow fibers, small turbulences are produced around the hollow fibers.

DETAILED DESCRIPTION OF THE PREFERRED EMBODIMENTS

Figure 1:
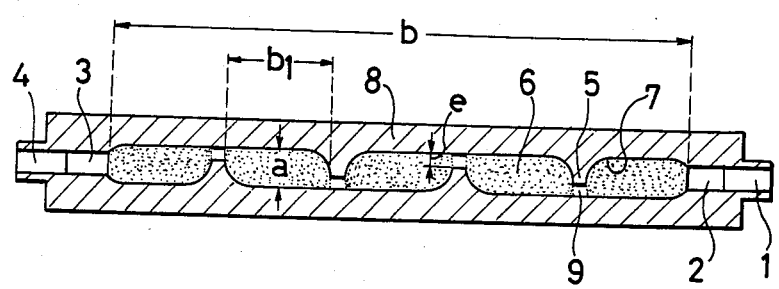
FIG. 1 is a vertical sectional view of a blood oxygenator embodying the present invention.
Figure 2:
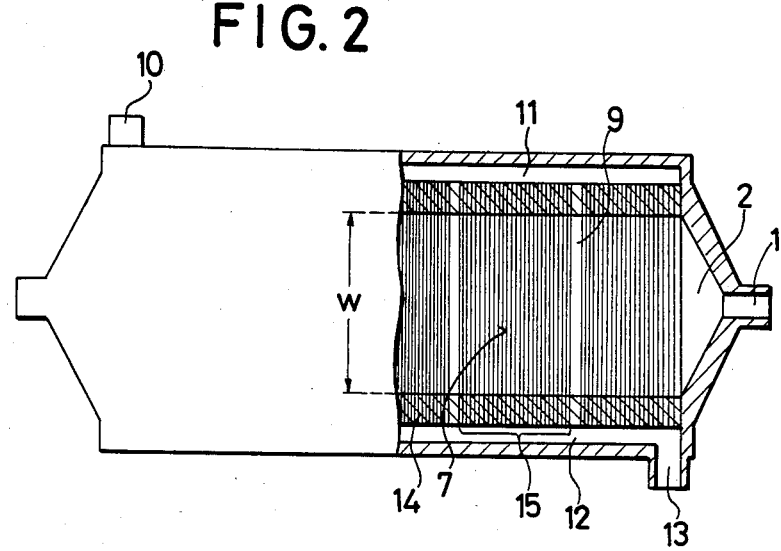
FIG. 2 is a partially cutaway plan view of the blood oxygenator of FIG. 1.

Referring first to FIG. 1, a blood inlet 1 and a blood flow uniforming chamber 2 are provided at one end of a housing 8, while a blood collection chamber 3 and a blood outlet 4 are provided at the other end. Positioned between the blood flow uniforming chamber 2 and the blood collection chamber 3 is a contact chamber which is divided into a plurality of compartments 6 with the interposition of blood flow channels narrowed by baffles 5. The contact chamber is packed with hollow fiber 7 of semipermeable membrane for use in gas exchange. Blood withdrawn from a human body (i.e., venous blood) passes through the blood inlet 1 and the blood flow uniforming chamber 2 and then enters the contact chamber. In the contact chamber, the venous blood is subjected to gas exchange with the gas in the bores of the hollow fibers 7 through the wall of the hollow fiber membrane, and converted into arterial blood. The resulting arterial blood passes through the blood collection chamber and leaves the blood oxygenator at the blood outlet. Although an exemplary blood oxygenator having the contact chamber divided into five compartments is shown in FIG. 1, the number of compartments 6 should be two or greater. Greater numbers of compartments are preferred from the viewpoint of the oxygenation rate. However, in consideration of the pressure loss and the ease of manufacture, it is practically desirable to divide the contact chamber into two to six compartments.

The relationships between the number of compartments constituting the contact chamber of the blood oxygenator and various characteristics of the blood oxygenator will now be described with reference to FIGS. 5 and 6.

Figure 5:
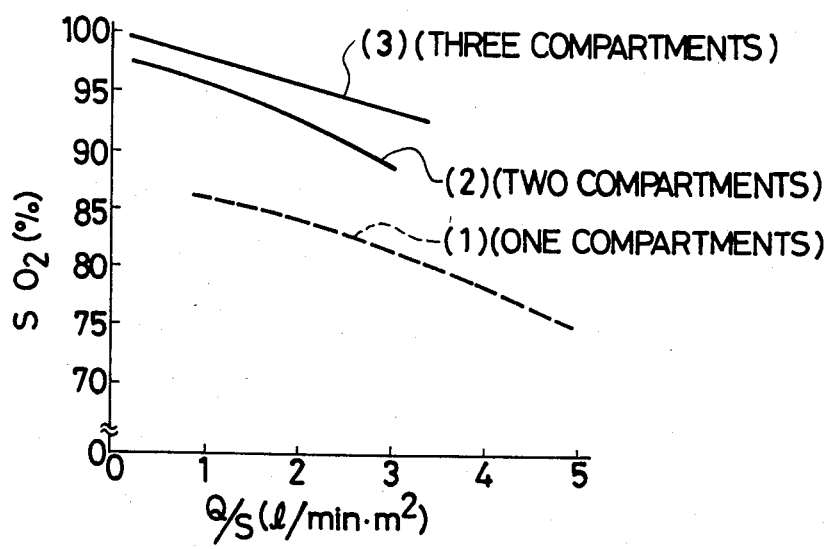
FIG. 5 is a graph showing the relationship between Q/S and the degree of outlet oxygen saturation of the blood (S $O_2$)

In FIG. 5, S $O_2$ on the ordinate indicates the degree of oxygen saturation of the blood, the saturation of all hemoglobin with oxygen being taken as 100%. Usually, the S $O_2$ of venous blood is about 60%. When a conventional blood oxygenator having a single contact chamber is evaluated, the degree of oxygen saturation of the blood is about 87% at a relatively low blood feed rate of about 1 liter per unit area of membrane, but is reduced to about 82% at an increased blood feed rate of 3 liters, as shown by curve (1) in FIG. 5. By contrast, with a blood oxygenator whose contact chamber is divided into two compartments by means of a baffle in accordance with the present invention, the degree of saturation of the blood is about 88% or higher even at a relatively high blood feed rate of about 3 liters, as shown by curve (2). When the contact chamber is divided into three compartments by means of two baffles, the degree of oxygen saturation is about 93% or higher. These results clearly indicate that the division of the contact chamber into a plurality of compartments has significantly beneficial effects.

Figure 6:
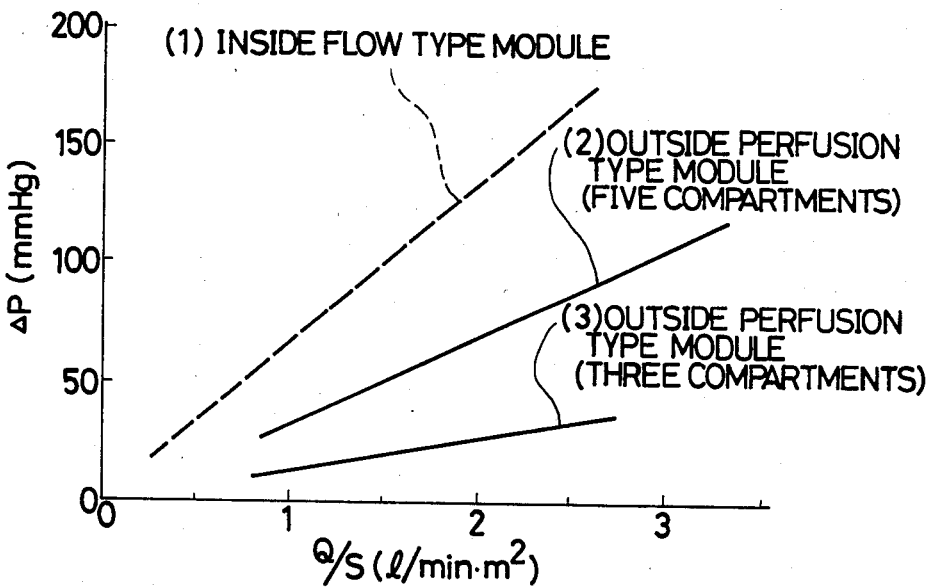
FIG. 6 is a graph showing the relationship between Q/S and the pressure loss for several type of blood oxygenators.

FIG. 6 is a graph showing the relationship between the blood feed rate and the pressure loss through the oxygenator for several types of blood oxygenators. Curve (1) indicates the results obtained with a blood oxygenator module of the conventional inside perfusion type in which blood is passed through the bores of the hollow fibers. It is evident from curve (1) that, in the module of this type, the pressure loss increases linearly as the blood feed rate per unit area of membrane (Q/S) becomes higher. Thus, this module is difficult to use because hemolysis tends to occur at higher blood feed rates. On the other hand, in a blood oxygenator of the present invention in which the contact chamber is divided into three compartments and blood is passed on the outside of the hollow fibers, only a slight increase in pressure loss is noted at higher blood feed rates, as shown by curve (3). Thus, a blood oxygenator exhibiting a very small pressure loss can be realized. Even in a blood oxygenator of the present invention in which the contact chamber is divided into five compartment by providing it with four baffles, it can be seen from curve (2) that the pressure loss is significantly small as compared with the conventional inside perfusion type module.

Figure 3:
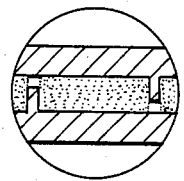
FIG. 3 is a sectional view illustrating several other forms of the blood flow channels narrowed by the baffles.
Figure 3:
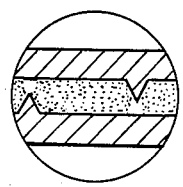
Figure 3:
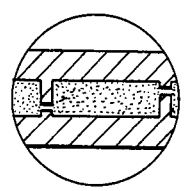
Figure 7:
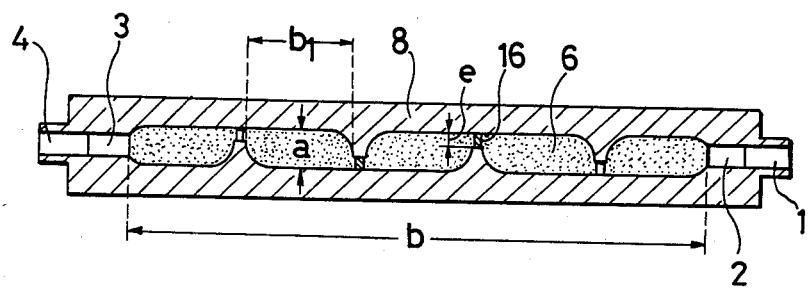
FIGS. 7 and 8 are views similar to FIGS. 1 and 2 showing a modified blood oxygenator having struts provided in the blood flow channels narrowed by the baffles.
Figure 8:
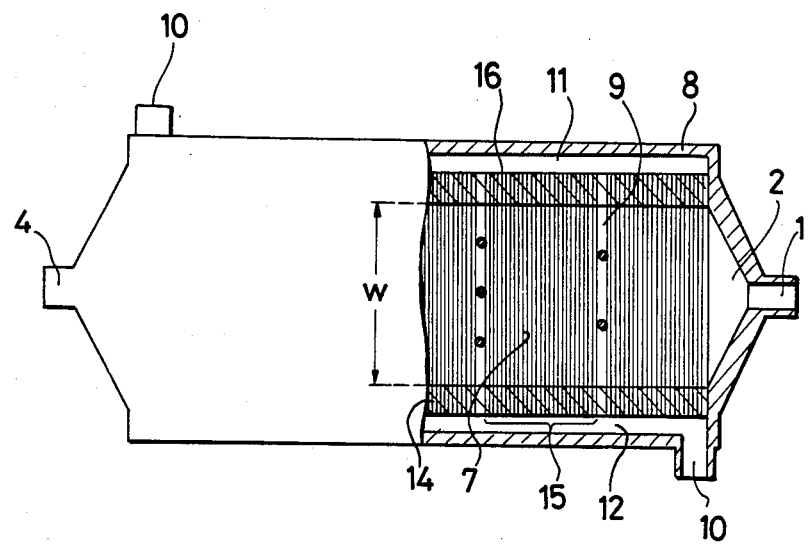

The baffles 5 may have any of various cross-sectional shapes including those shown in FIG. 3, provided that they can allow for narrowed blood flow channels. However, baffles having a curved cross section as shown in FIG. 1 are preferably used in order to avoid stagnation of the blood. The blood flow channels narrowed by the baffles produce turbulences in the flow of blood to create a uniform distribution of the gas concentration in the blood and to prevent channeling of the blood, and it is preferable to position the baffles alternately on the upper and lower sides. In this case, one or more struts 16 are preferably provided at the free end of each baffle (i.e., in each of the narrowed blood flow channel), as shown in FIGS. 7 and 8.

The dimensions of the contact chamber will next be described. It is preferable that the length ($b_1$) of each compartment as measured in the direction of blood flow be equal to or larger than the maximum thickness (a) of the compartment. If the thickness (a) is larger than the length ($b_1$), the flow of blood in the direction of the thickness will be so dominant that stagnation of the blood will tend to occur at the corners of the baffles, entrained air bubbles can hardly be removed, and an increase in pressure loss may result. Preferably, the contact chamber is generally in the form of a box whose overall length (b) is 2 to 30 times as large as its thickness (a).

The thickness (e) of the blood flow channels 9 narrowed by the baffles 5 is preferably equal to or smaller than one-half the thickness (a) of the compartments. Each end of the bundle of hollow fibers 15 is secured together by means of a potting material 14 (such as polyurethane) in such a way that the bores of the hollow fibers are left open and the inside of the hollow fibers is separated from the outside thereof. One of the lateral spaces separated by the potting material and communicating with the bores of the hollow fibers constitutes a gas distribution passage 11 and communicates with the gas inlet 10. The other lateral space constitutes a gas collection passage 12 and communicates with the gas outlet 13. Oxygen or an oxygen-containing gas is introduced from the gas inlet 10 and passed through the bores of the hollow fibers, where it undergoes gas exchange with the blood through the medium of the hollow fiber membrane. The resulting gas, which has been decreased in oxygen content and increased in carbon dioxide content, leaves the blood oxygenator at the gas outlet 13. The width (w) of the compartments (i.e., the distance between both masses of potting material) should be determined in relation to the blood flow rate and the thickness (a) of the compartments. However, it is preferable that the width (w) be 1 to 20 times as large as the thickness (a). If the width (w) is smaller than the thickness (a), the surfaces of the potting material will exert a significant influence on the blood and, therefore, may produce undesirable results. If the width (w) is larger than 20 times the thickness (a), it will become difficult to distribute the blood uniformly to the surfaces of all hollow fibers, and thereby to prevent channeling of the blood.

A plurality of blood oxygenators in accordance with the present invention may be connected in parallel in order to oxygenate blood at higher flow rates.

The present invention is further illustrated by the following example and comparative example:

EXAMPLE AND COMPARATIVE EXAMPLE

Figure 4:
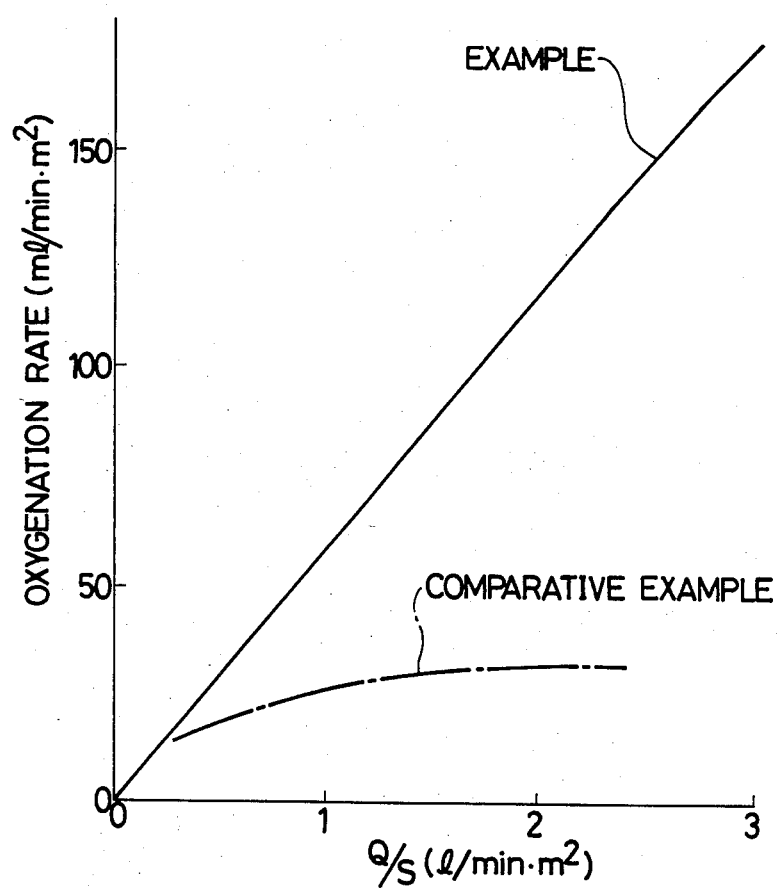
FIG. 4 is a graph showing the relationship between the blood feed rate per unit area of membrane (Q/S) and the oxygenation rate in an example of the present invention and a comparative example, the oxygenation rate being plotted as ordinate and Q/S as abscissa.

Using microporous polypropylene hollow fiber membrane having a wall thickness of 22 μm, an internal diameter of 200 μm and a bubble point of 12.5 kg/cm$^2$ in ethanol, two blood oxygenators were constructed according to the specifications given in Table 1. These blood oxygenators were comparatively tested by passing bovine blood and pure oxygen therethrough. The bovine blood had a hematocrit of 35%, a pH of 7.32, an oxygen partial pressure of 65 mmHg, a carbon dioxide partial pressure of 45 mmHg and a hemoglobin concentration of 12.5 g/dl. The pure oxygen was preheated to 37° C. and fed at a flow rate of 2 liters/min. The results thus obtained are shown in FIG. 4 where the oxygenation rate (in ml/min.m$^2$) is plotted against the blood feed rate per unit area of hollow fiber membrane (Q/S in liters/min.m$^2$).

The blood oxygenator of the Example was superior because of its freedom from channeling of the blood and the gas. Moreover, it can be seen from FIG. 4 that the blood oxygenator of the Example was also superior from the viewpoint of oxygenation rate. The blood oxygenator of the Example exhibited a high carbon dioxide performance of about 100 ml/min.m$^2$ at Q/S being 2 l/min.m$^2$.

TABLE 1

| | |
|---|---|
| Example | A blood oxygenator of the construction shown in FIG. 1 which was characterized in that a = 0.8 cm, $b_1$ = 1.8 cm, e = 0.2 cm, w = 20.0 cm, the number of compartments was 5, the degree of packing of the hollow fibers in each compartment was 30%, and the total area of membrane was 0.5 m$^2$. |
| Comparative Example | A blood oxygenator of the same construction as in the Example, except that no baffle was provided (i.e., the contact chamber comprised a single compartment) and the direction of blood flow was at an angle of about 30° with the bundle of hollow tubes. |

As described above, the blood oxygenator of the present invention has superior performance in that it has high oxygen and carbon dioxide exchange rates per unit area of membrane, causes little channeling of the blood and the gas, and exhibits only a small pressure loss in the flow of blood. Moreover, the blood oxygenator of the present invention has additional advantages in that it is inexpensive because of its ease of manufacture and the extracorporeal blood volume is small enough to alleviate the burden imposed on the patient.

What is claimed is:

1. A blood oxygenator comprising:

a housing having a blood inlet, a blood outlet, a gas inlet, a gas outlet, and a blood-gas contact chamber therein, said chamber having an entrance in communication with said blood inlet and an exit in communication with said blood outlet, said chamber having an overall length (b) as measured in a direct line between said entrance and said exit, an overall width (w) measured in a direction perpendicular to said direct line, and an overall thickness (a) measured in a direction perpendicular to both said overall length and said overall width;

bundles of semi-permeable hollow fiber membrane disposed in said chamber and extending across said width (w) thereof, said membrane being made of a material suitable for the oxygenation of blood; and a potting material securing together opposite ends of said bundles in such a way as to allow their open ends to communicate respectively with said gas inlet and said gas outlet, the space around said bundles communicating with said blood inlet and said blood outlet, wherein a blood flow path is established from said blood inlet, through said chamber and to said blood outlet, said oxygenator further comprising means for minimizing hemolysis of blood flowing along said blood flow path, said means for minimizing hemolysis comprising blood flow restriction means in the form of at least one baffle extending into said blood flow path in the direction of said thickness of said chamber and forming a plurality of compartments in said chamber, said at least one baffle extending substantially parallel to said bundles, the location of said at least one baffle with respect to said length of said chamber being such that the maximum thickness (a) of each said compartment formed by said at least one baffle is no greater than the length ($b_1$) of each said compartment as measured in the direction of said length of said chamber.

2. A blood oxygenator comprising:

a housing generally in the form of a box and having a blood inlet, a blood outlet, a gas inlet, a gas outlet, and a blood-gas contact chamber therein, said chamber having an entrance in communication with said blood inlet and an exit in communication with said blood outlet, said chamber having an overall length (b) as measured in a direct line between said entrance and said exit, an overall width (w) measured in a direction perpendicular to said direct line, and an overall thickness (a) measured in a direction perpendicular to both said overall length and said overall width;

bundles of semi-permeable hollow fiber membrane disposed in said chamber, said membrane being made of a material suitable for the oxygenation of blood; and sections of a potting material respectively securing together opposite ends of said bundles in such a way as to allow their open ends to communicate respectively with said gas inlet and said gas outlet, said sections of potting material being disposed on opposite sides of said chamber, extending substantially in the direction of said overall length and establishing said overall width (w) of said chamber as being the distance across said chamber between said sections of potting material, the space around said bundles communicating with said blood inlet and said blood outlet, said chamber being divided into a plurality of compartments by the interposition of at least one baffle projecting into said chamber to form a narrow blood flow channel, said at least one baffle projecting into said chamber substantially in the direction of a thickness of said chamber and also extending in a direction substantially parallel to said bundles, wherein the length ($b_1$) of each compartment as measured in the direction of said overall length of said chamber is equal to or greater than the maximum thickness (a) of said compartment as measured in the direction of said thickness of said chamber.

3. The blood oxygenator of claim 2 wherein one or mre struts are provided at the free end of each of said baffles.

4. The blood oxygenator of claim 2 wherein overall length of said contact chamber (b) is 2 to 30 times as great as its thickness (a).

5. The blood oxygenator of claim 2 wherein said contact chamber is divided into two to six compartments with the interposition of blood flow channels narrowed by said baffles.

6. The blood of oxygenator of claim 2 or 5 wherein the degree of packing of said semipermeable hollow fiber membrane in said contact chamber ranges from 20 to 40%.

7. The blood oxygenator of claim 2 or 5 wherein said blood inlet and blood outlet are provided in such a way that the direction of blood flow is substantially perpendicular to the direction of gas flow through the bores of said semipermeable hollow fiber membrane disposed in said contact chamber as well as substantially perpendicular to said baffles.

* * * * *